US007967010B2

(12) United States Patent
Vedrine et al.

(10) Patent No.: US 7,967,010 B2
(45) Date of Patent: *Jun. 28, 2011

(54) SPRAY OR INJECTION DEVICE ALLOWING AT LEAST TWO PRESET DOSES OF PRODUCT TO BE DELIVERED

(75) Inventors: Lionel Vedrine, Ridgewood, NJ (US); Frederic Perot, Saint Paul de Varces (FR); Laurent Barrelle, Saint Nizier du Moucherotte (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/690,159

(22) Filed: Jan. 20, 2010

(65) Prior Publication Data

US 2010/0212663 A1 Aug. 26, 2010

Related U.S. Application Data

(63) Continuation of application No. 10/529,050, filed on Sep. 26, 2003.

(30) Foreign Application Priority Data

Sep. 27, 2002 (FR) ...................................... 02 12002

(51) Int. Cl.
*B05B 7/00* (2006.01)
*B05B 11/00* (2006.01)
(52) U.S. Cl. ......... 128/200.19; 128/200.14; 128/200.17; 128/207.18; 604/208; 604/220; 604/234
(58) Field of Classification Search ............. 128/200.14, 128/200.17, 200.19, 207.18; 604/208, 220, 604/234
See application file for complete search history.

(56) References Cited

U.S. PATENT DOCUMENTS

| 2,648,334 | A | | 8/1953 | Brown et al. |
| 4,583,978 | A | | 4/1986 | Porat et al. |
| 4,758,232 | A | * | 7/1988 | Chak ............................ 604/220 |
| 4,929,230 | A | | 5/1990 | Pfleger |
| 4,962,868 | A | | 10/1990 | Borchard |
| 5,271,527 | A | * | 12/1993 | Haber et al. .................... 222/43 |
| 5,298,024 | A | * | 3/1994 | Richmond ...................... 604/90 |
| 5,427,280 | A | | 6/1995 | Fuchs |
| 5,601,077 | A | | 2/1997 | Imbert |
| 5,704,921 | A | * | 1/1998 | Carilli ........................... 604/198 |
| 5,722,956 | A | * | 3/1998 | Sims et al. .................... 604/131 |
| 5,951,526 | A | | 9/1999 | Korisch et al. |
| 6,382,204 | B1 | | 5/2002 | Jansen et al. |
| 6,382,465 | B1 | | 5/2002 | Greiner-Perth |
| 6,427,878 | B1 | * | 8/2002 | Greiner-Perth et al. ...... 222/391 |
| 7,681,570 | B2 | * | 3/2010 | Vedrine et al. ........... 128/200.14 |

FOREIGN PATENT DOCUMENTS

EP 1 129 786 9/2001

* cited by examiner

*Primary Examiner* — Justine R Yu
*Assistant Examiner* — Clinton Ostrup
(74) *Attorney, Agent, or Firm* — David M. Fortunato; Cohen Pontani Lieberman and Pavane LLP

(57) ABSTRACT

A spray or injection device that includes a casing or a pusher that includes at least one tab radially moveable between a first radial position, in which the tab does not impede the movement of the pusher with respect to the casing, and a second radial position in which the tab opposes movement of the pusher. The pusher or the casing, respectively, includes at least one ramp-shaped projection configured to bring the tab into the second radial position and then allow it to return to the first radial position. The pusher or the casing further includes at least one stop between the pusher and casing to delineate the end of a first stroke corresponding to a first dose of medicament, and the beginning of a second stroke corresponding to a second dose of medicament.

14 Claims, 19 Drawing Sheets

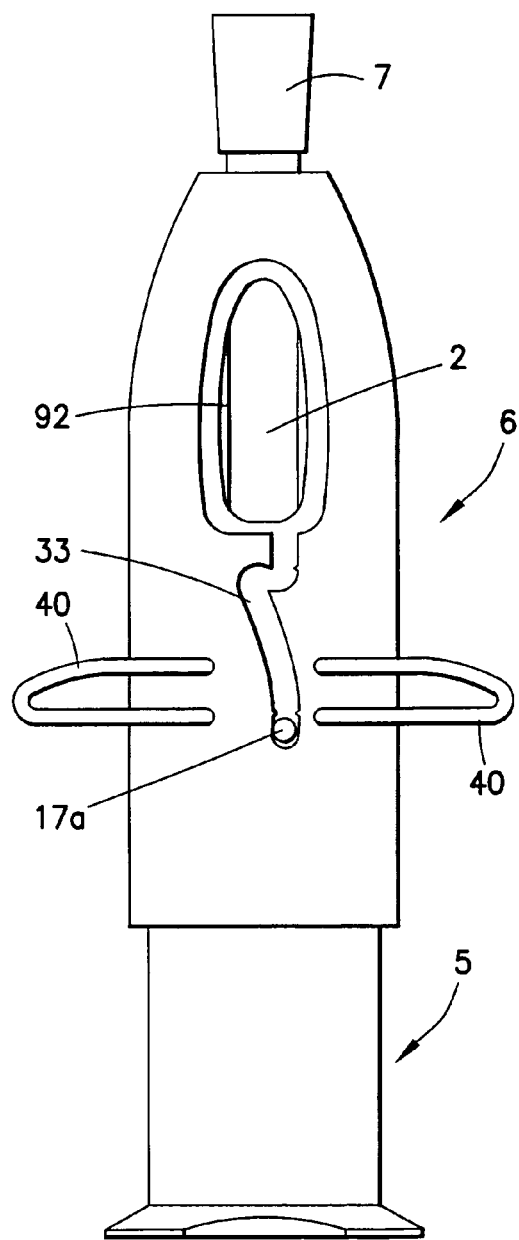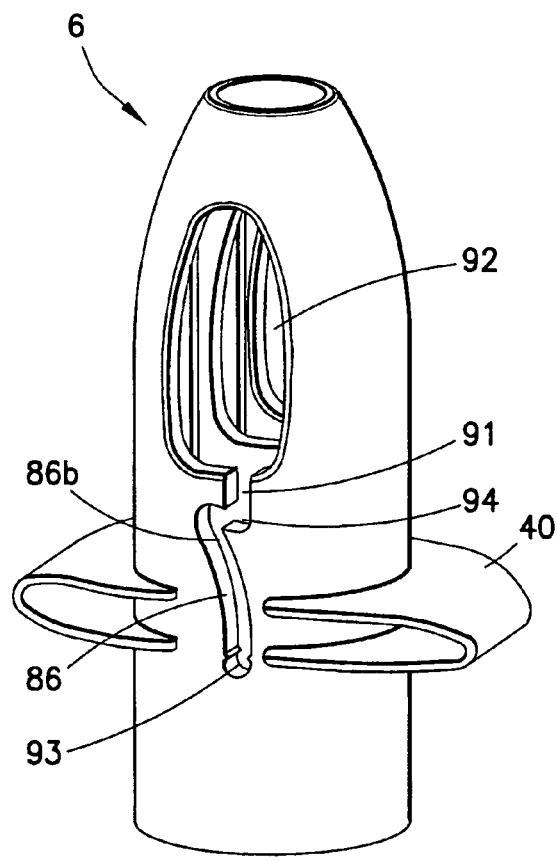
FIG.18
FIG.19

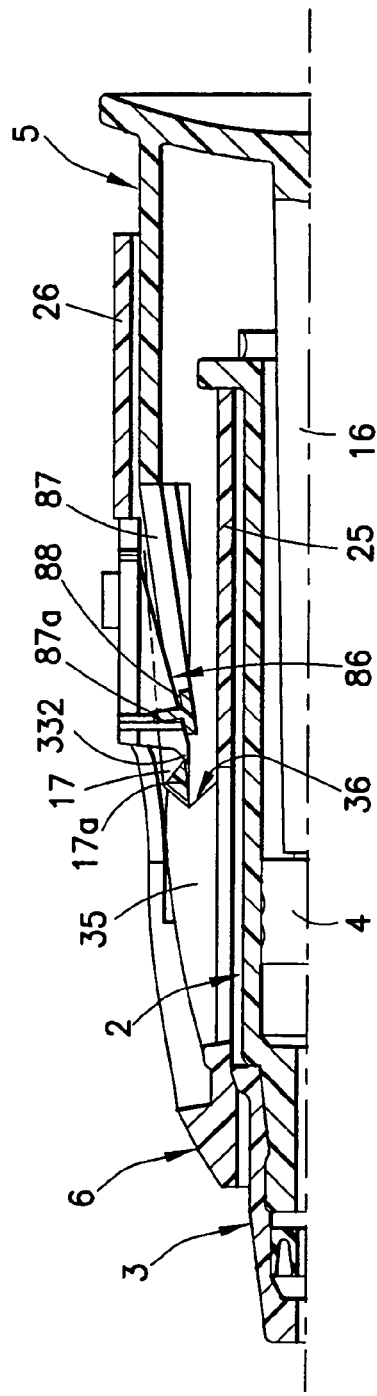
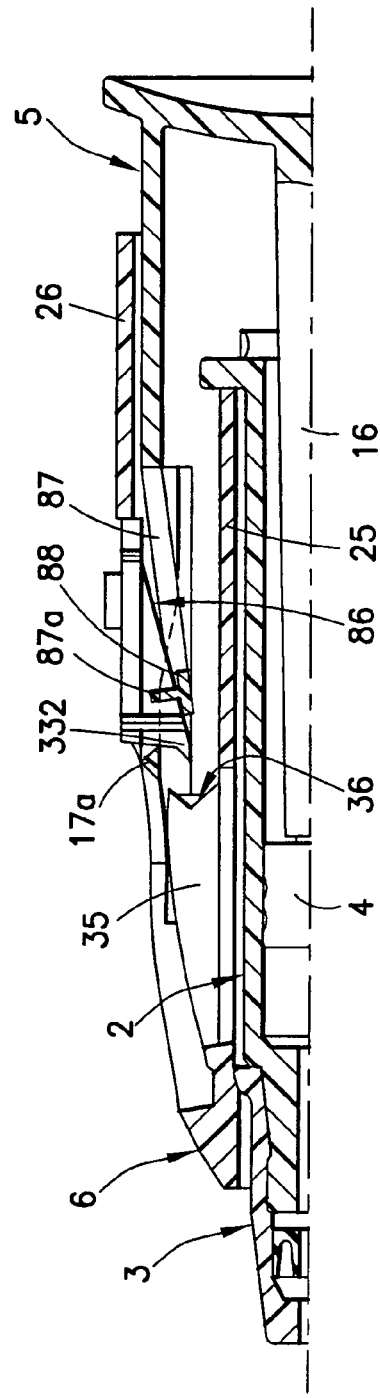
FIG.27
FIG.28

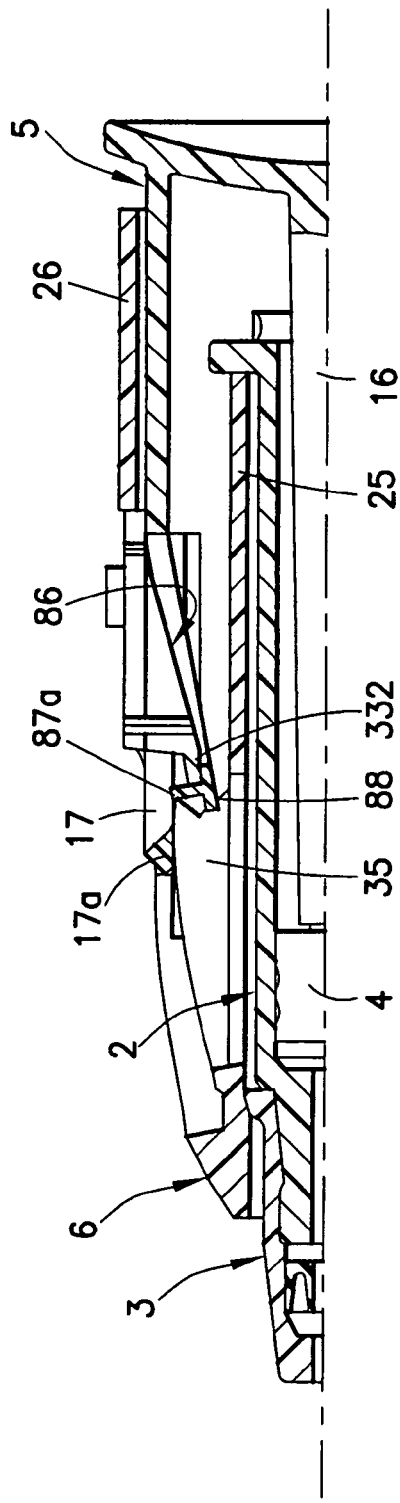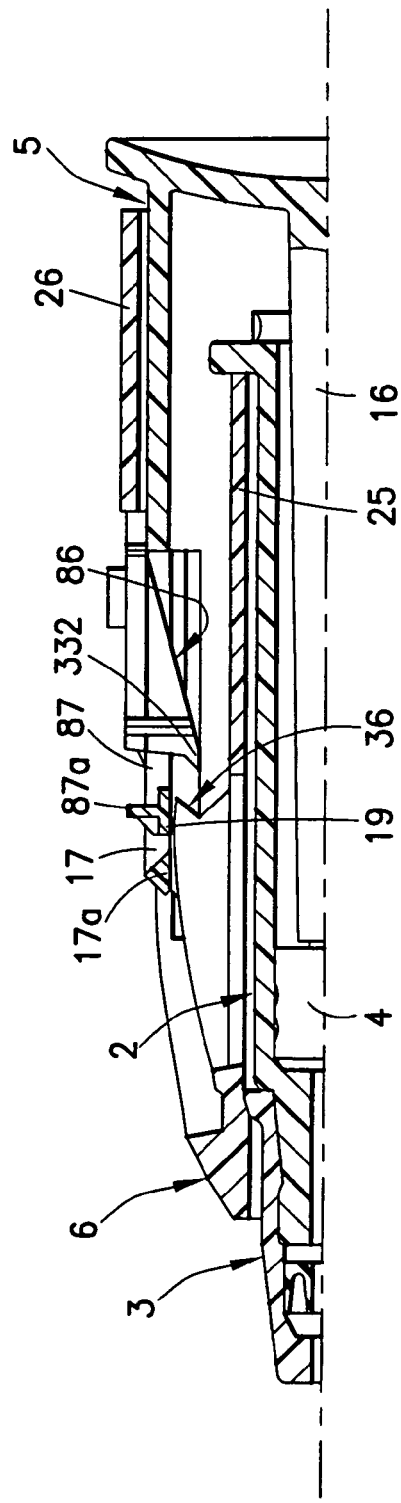

SPRAY OR INJECTION DEVICE ALLOWING AT LEAST TWO PRESET DOSES OF PRODUCT TO BE DELIVERED

CROSS REFERENCE TO RELATED APPLICATIONS

This application is a continuation of U.S. patent application Ser. No. 10/529,050 which was filed with the U.S. Patent and Trademark Office on Sep. 26, 2003, which is a U.S. National Stage of International Application No. PCT/FR03/02836 filed on Sep. 26, 2003, which claims priority from French Application No. 02/12002 filed on Sep. 27, 2002, the entire content of which is incorporated by reference.

BACKGROUND OF THE INVENTION

1. Field of the Invention

The present invention relates to a spray or injection device for spraying or injecting a product of interest in liquid form, making it possible to deliver at least a first dose and a second dose of said product in succession. The invention is especially applicable to a nasal spray making it possible to deliver two doses, one for each nostril.

2. Description of the Related Art

It is known to produce a nasal spray based on the general structure of a syringe, comprising detachable stop means. These stop means make it possible, when they are in place, to define a portion of travel of the plunger rod, in order to deliver a first dose, and may be withdrawn or removed in order to free the rest of the travel of the plunger rod, to allow the delivery of the second dose. U.S. Pat. Nos. 5,601,077 and 5,951,526, in the name of the Applicant, illustrate this technique.

U.S. Pat. No. 6,382,204, also in the name of the Applicant, also discloses the producing of a device comprising a casing receiving the syringe body and a pusher forming the plunger rod, the casing comprising lugs and the pusher comprising grooves in which these lugs can slide. Each groove comprises two longitudinal portions offset at an angle and an intermediate portion connecting these two longitudinal portions, perpendicular to the axis of the pusher. Each lug is able to slide in a first longitudinal portion until it comes into abutment against the pusher in the region for connecting this first longitudinal portion to the intermediate portion then, by axial rotation of the pusher, take the intermediate portion until it comes opposite the second longitudinal portion, and then slide in this second longitudinal portion. Said longitudinal portions thus define two successive portions of travel of the pusher, determining the delivery of the first and second doses of product, respectively.

The existing devices have the drawback of not being very easy to manipulate, whether in terms of removing said stop means according to the first technique cited or in terms of performing the relative pivoting of the pusher and of the casing according to the second technique cited.

These devices also have the drawback of not preventing errors in use.

Furthermore, the design of the aforementioned grooves and lugs is relatively complex to achieve in order to obtain good operational reliability.

SUMMARY OF THE INVENTION

The present invention aims to overcome all these drawbacks, by supplying a device which is easy to manipulate, while reducing errors of use to a minimum and retaining a relatively simple structure which is inexpensive to manufacture.

Accordingly, a spray or injection device is provided for spraying or injecting a product of interest, in liquid form. The device is configured to deliver at least a first and a second preset dose of the product in succession. The device extends along a reference axis from a distal end to a proximal end and comprises an axially elongate container containing the product, and a plunger disposed in and blocking off the container. Movement of the plunger allows the product to be propelled distally from the container. A casing having a stop surface is provided and accommodates and axially secures the container. A pusher is assembled with the casing such that the pusher and casing are moveable with respect to each other. The pusher has a stop surface and is configured to move the plunger within the container in the reference direction wherein the stop surface engages the stop surface of the casing to form a stop when the plunger is advanced a certain distance in the container. The stop defines a length of travel of the pusher with respect to the casing so as to divide the length of travel of the pusher into a first travel portion corresponding to the delivery of the first preset dose, and a second travel portion corresponding to the delivery of the second preset dose, wherein the stop surface of the pusher and the stop surface of the casing are configured to allow disengagement therebetween when a force applied to the pusher in the reference direction is reduced and, without any rotational movement of the pusher or casing, the pusher can then be advanced along the second travel portion for delivery of the second preset dose.

Thus, it is enough for the user to exert a force on the pusher so as to move this pusher with respect to the casing in order to free a first dose of product, until the movement of the pusher is blocked against the stop, then to reduce this force to free the stop and to make it possible, by an increased force on the pusher, to deliver the second or following dose of product.

The handling of the device according to the invention therefore does not involve any withdrawal or removal of the stop means nor axial rotation of the pusher with respect to the casing, and is therefore particularly easy. The operation of the device eliminates virtually any risk of error of use, and the design of this device is simpler than that of a device according to the prior art.

Advantageously, the casing and the pusher comprise means making it possible to form at least one "hard point" having to be crossed at the start of delivering a dose. These means make it possible to prevent any unintentional spraying or injection of a dose, and therefore to make the use of the device even more reliable. These means may especially consist of at least one lug projecting laterally from a tab and of at least one boss made in a corresponding location of the casing or the pusher.

BRIEF DESCRIPTION OF THE DRAWINGS

In the drawings, like reference characters refer to the same parts throughout the different views. Also, the drawings are not necessarily drawn to scale.

FIG. 18 is a front-on view of a device according to a third embodiment of the present invention;

FIG. 19 is a perspective view of the casing of the device according to FIG. 18;

FIGS. 25 to 30 show, in axial half-section, various stages in the operation of the pusher with respect to the casing, namely, respectively:

FIG. 25 shows an axial half-section view of an initial position, prior to delivery of the first dose of the pusher with respect to the casing;

FIG. 26 shows an axial half-section view of flexing of the tab with the tongue remaining in a normal position;

FIG. 27 shows an axial half-section view of flexing of the tab and of the tongue;

FIG. 28 shows an axial half-section view of escape of the tab from the ramp, with flexing of the tongue;

FIG. 29 shows an axial half-section view of continued movement of the tab, with the tongue escaping from the ramp, to deliver the second dose;

FIG. 30 shows an axial half-section view of continued movement of the tab and the tongue, beyond the ramp.

DETAILED DESCRIPTION OF THE PRESENTLY PREFERRED EMBODIMENTS

Figure 1:
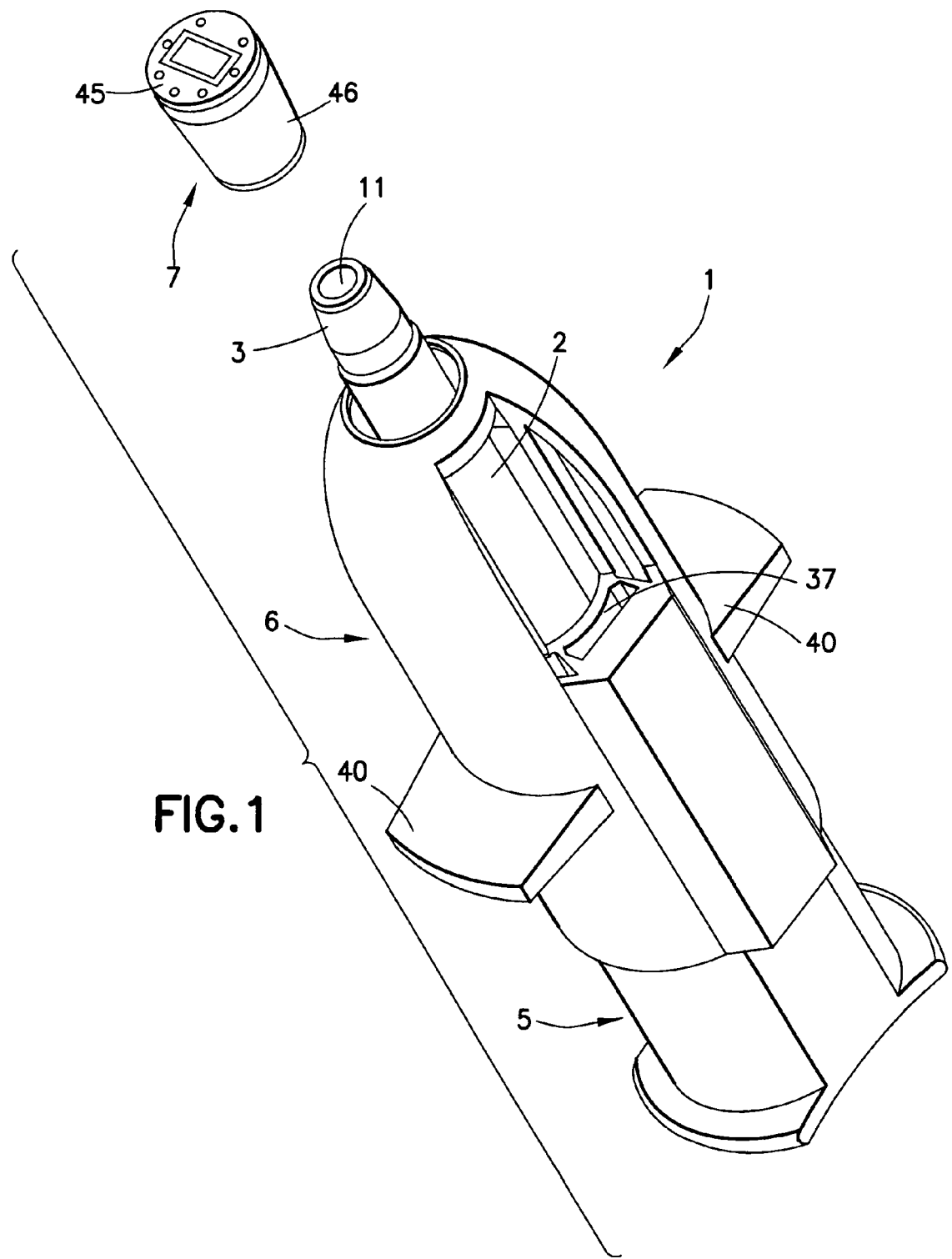
FIG. 1 is a perspective view thereof according to a first embodiment.

FIGS. 1 to 8 show a nasal spray device 1 according to a first embodiment of the invention making it possible to deliver two preset doses of a product of interest, in liquid form, one for each nostril.

This device 1 comprises a syringe body 2, a spray nozzle 3, a plunger 4, a pusher 5, a casing 6 and a protective lid 7.

The syringe body 2 is of conventional type, for example made of glass, with a proximal collar 10 and a distal flow conduit 80.

The nozzle 3 is fitted onto the distal end of the syringe body 2. It forms a spray head 11 making it possible to spray the product contained in the syringe body 2, and comprises a proximal collar 12. Since such a nozzle 3 is known per se, it is not described further in detail.

The plunger 4 is also of conventional type, being a syringe plunger.

Figure 2:
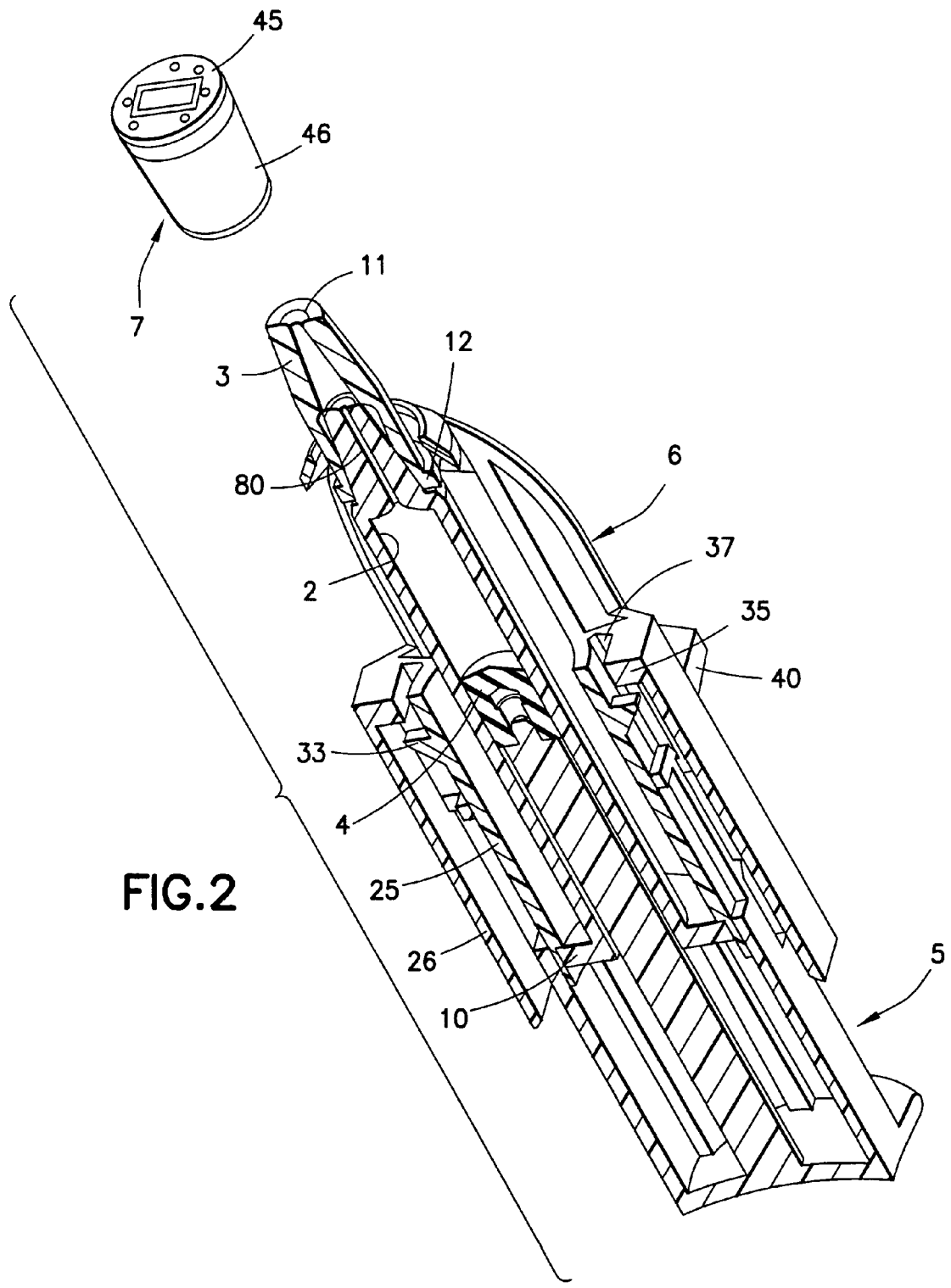
FIG. 2 is a view thereof similar to FIG. 1, in axial section.
Figure 3:
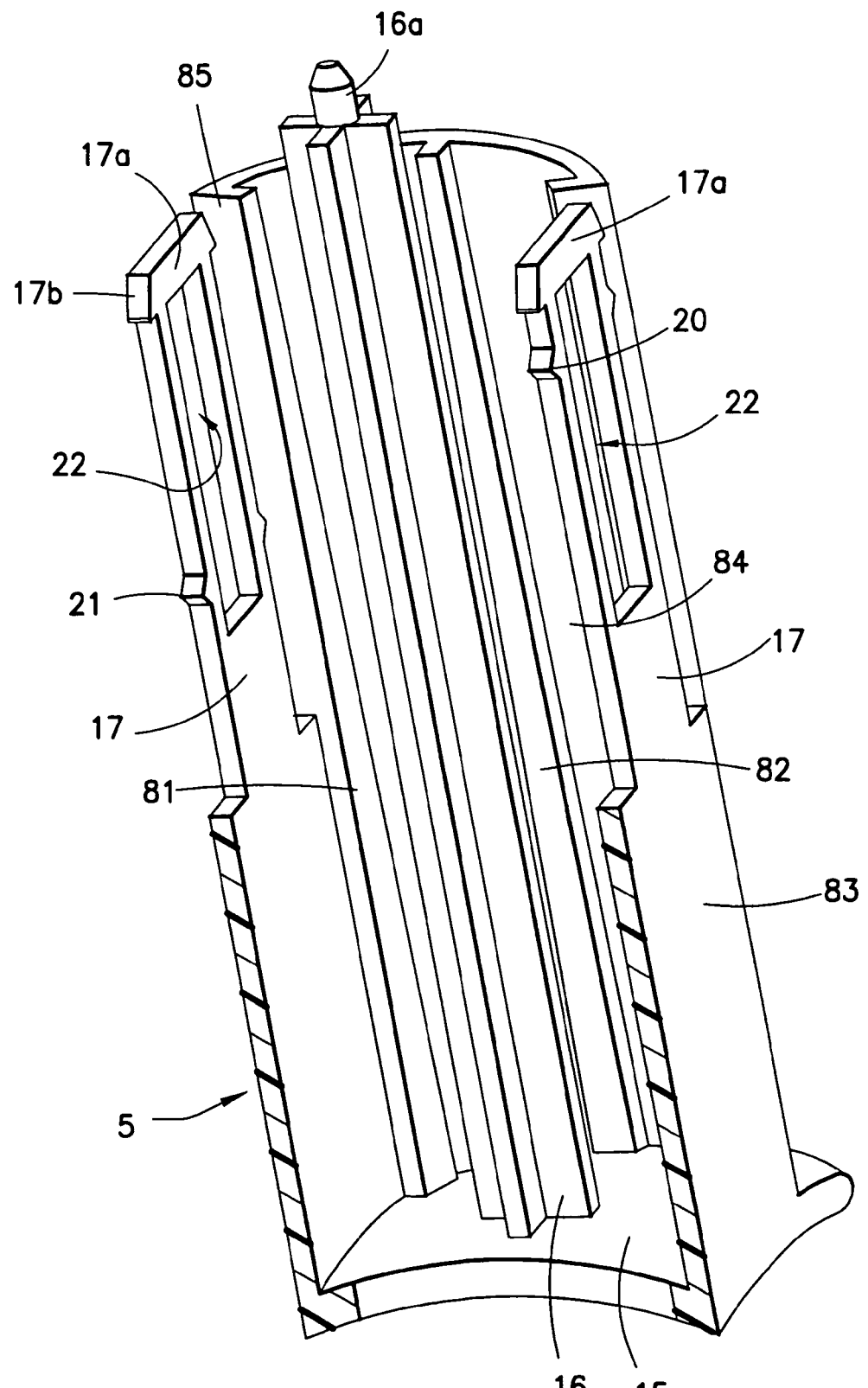
FIG. 3 is a view in partial section of the pusher which it comprises.

As is shown more particularly in FIGS. 2 and 3, the pusher 5 has a generally hollow cylindrical shape, closed by a proximal bottom 15, and comprises an axial rod 16 secured to this bottom 15, accommodating the plunger 4 at its distal end by virtue of a stud 16a which it comprises. The wall 83 of the pusher 5 is stiffened by longitudinal internal ribs 81 and 82 parallel to the rod 16.

The pusher 5 also comprises, in the example shown, four cuts 84, 85 made longitudinally from its distal end, defining two diametrically opposed moveable tabs 17. The whole pusher 5 is made from a slightly flexible common plastic, the radial or tangential mobility of the tabs 17 resulting from the flexibility of this material. This flexibility provides the mobility of the tabs 17 between a first, undeformed, inner, unstressed, radial normal position, shown in FIGS. 2, 3, 5, 7 and 8, and a second, stressed, outer, flexed, radial position, shown in FIG. 6, in which these tabs 17 are elastically deformed.

Each tab 17 has a distal head or pressing region 17a with projecting edges 17b, forming, with a complementary means comprised in the casing 6, that is a boss 38 in the example shown, snap-fastening means making it possible to prevent the separation of the pusher 5 from the casing 6 after engagement of the pusher in the casing, as will become apparent further on.

The tabs 17 further comprise two pairs of lugs 20, 21 projecting laterally, located, from one tab to the other, at two different heights. These lugs 20, 21 define, with the corresponding bosses 38 made in the casing 6, "hard points" having to be crossed at the start of spraying a dose, as will also be explained further on.

Each tab 17 also comprises a window or nonpressing region 22 made through it, set back from a pressing region 17a; this window stretches axially over a preset length.

Figure 4:
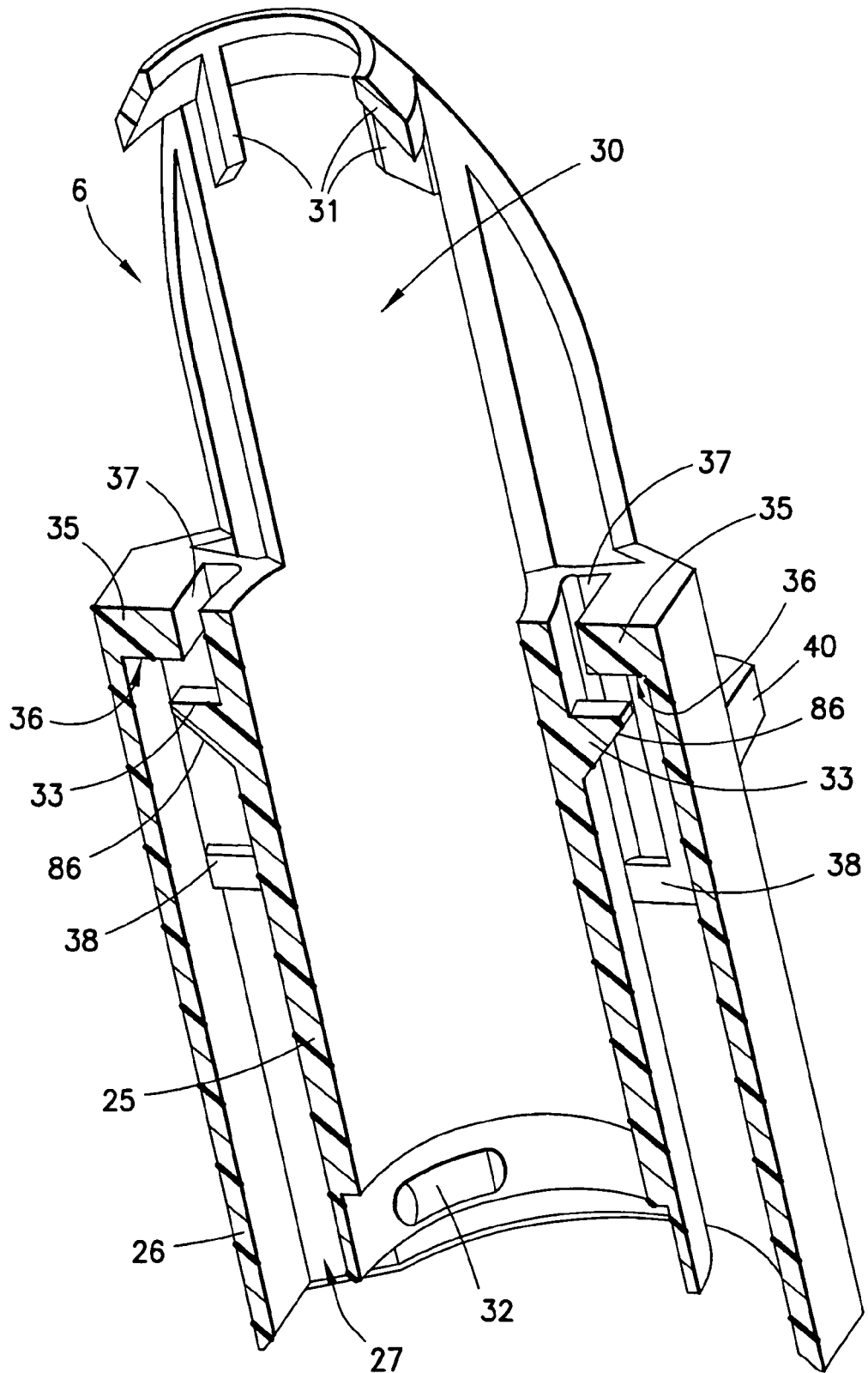
FIG. 4 is a view in axial section of the casing which it comprises.

As shown in FIGS. 2 and 4, the casing 6 comprises two walls 25, 26 joined together at the distal end of this casing, these walls 25, 26 defining between them a space 27 in which the pusher 5 is designed to be engaged so that it can slide.

The inner wall 25 defines a housing 30 for accommodating and axially securing the syringe body 2 and the spray nozzle 3, the casing 6 comprising distal tabs 31 which make it possible to center the nozzle 3 and the distal end of the syringe body 2, together with proximal bosses 32 for snap-fastening the collar 10 of the syringe body 2.

This inner wall 25 also comprises, in the example shown, two projections 33 each comprising an oblique ramp facing toward the distal end of the device 1 and diametrically opposed, projecting from its outer face, these projections 33 being designed to cooperate with the tabs 17 of the pusher 5, as will become apparent further on. These projections also have a shape tailored to penetrate freely and slide with respect to a window 22, as described hereinbelow.

Figure 17:
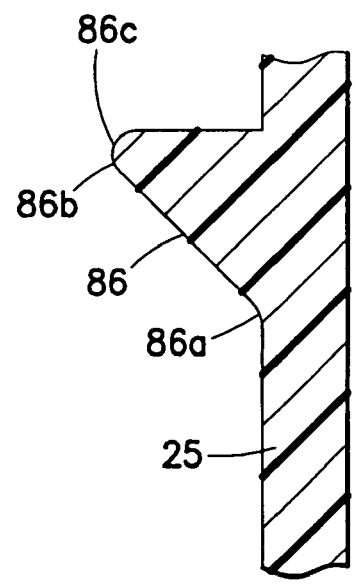
FIG. 17 shows, in an enlarged view, a detail regarding the ramp belonging to the casing of the device according to the first embodiment (FIGS. 1 to 8) of the invention.

As can be seen more clearly in FIG. 17, the ramps 86 have anterior edges 86c (those facing toward the tabs 17) that are rounded, and shaped to be encountered by the tabs 17 only at the end of the spraying or injection of the first dose. This then prevents friction from being generated at the start of the spraying or injection of the first dose, when the pusher speed is low.

The outer wall 26 comprises two returns 35 forming, inside said space 27 and at a preset distance from the projections 33, internal stops 36 against which the distal heads 17a of the tabs 17 may respectively abut, as will also be explained further on.

These returns 35 also comprise two openings 37 which allow the tabs 17 to pass therethrough by sliding in axial translation.

The outer wall 26 further comprises the two inner bosses 38, beyond which the heads 17a of the tabs 17 snap-fasten via their projecting edges 17b in order to prevent the separation of the pusher 5 from the casing 6, and with which the lugs 20, 21 cooperate in order to form the aforementioned hard points.

The outer wall 26 also comprises, in the example shown, two diametrically opposed outer tabs 40 projecting from its outer face, serving to support two fingers of the user when exerting, on the casing 6, a force opposing the pressure exerted on the bottom of the pusher 5 by another finger of the user.

As for the lid 7, it has a transverse end wall 45 and a peripheral wall 46 which allows it to cover the part of the nozzle 3 that extends beyond the casing 6.

Figure 5:
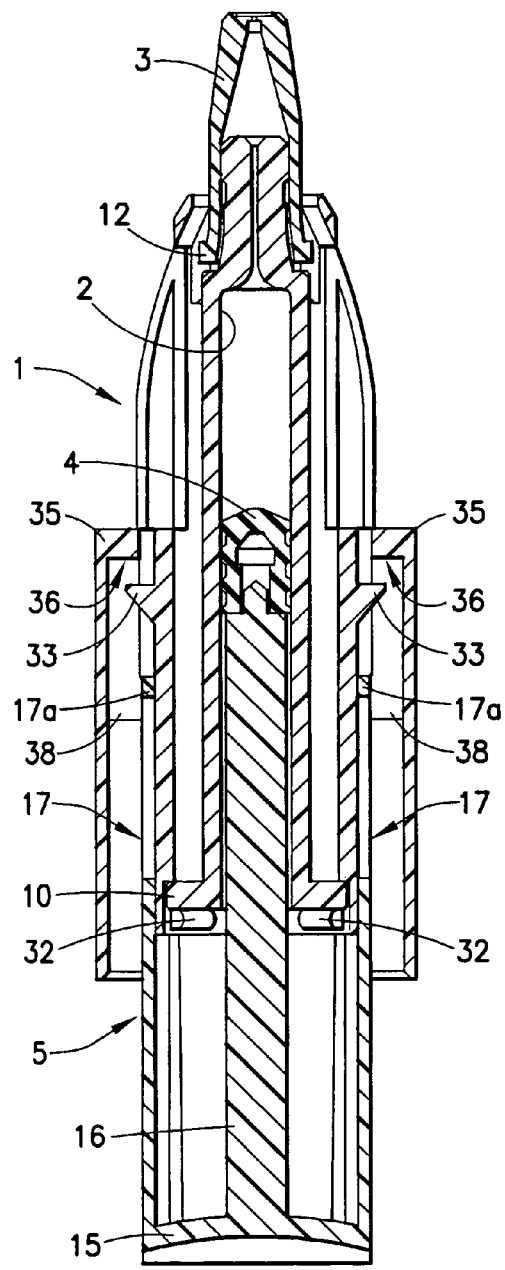
FIGS. 5 to 8 are views thereof in axial section of the device according to the first embodiment, respectively at the start of injecting a first dose, at the end of injecting this first dose, at the start of injecting the second dose and at the end of injecting this second dose.

FIG. 5 shows the device 1 at the start of the phase of spraying a first dose of product. Opposing forces are exerted on the pusher 5 and on the outer tabs 40 in order to make the aforementioned lug 20 of a tab 17 cross the corresponding boss 38 then to make the pusher 5 slide with respect to the casing 6, thus spraying the first dose.

During this movement, the heads or pressing regions 17a of the tabs 17 come against the ramps 86 of the projections 33, respectively, which moves these tabs 17 toward their abovementioned second, radially outer positions through the sliding of each of the heads 17a from an end known as the initial end 86a to an end known as the final end 86b of a ramp 86; cf. FIG. 17.

Figure 6:
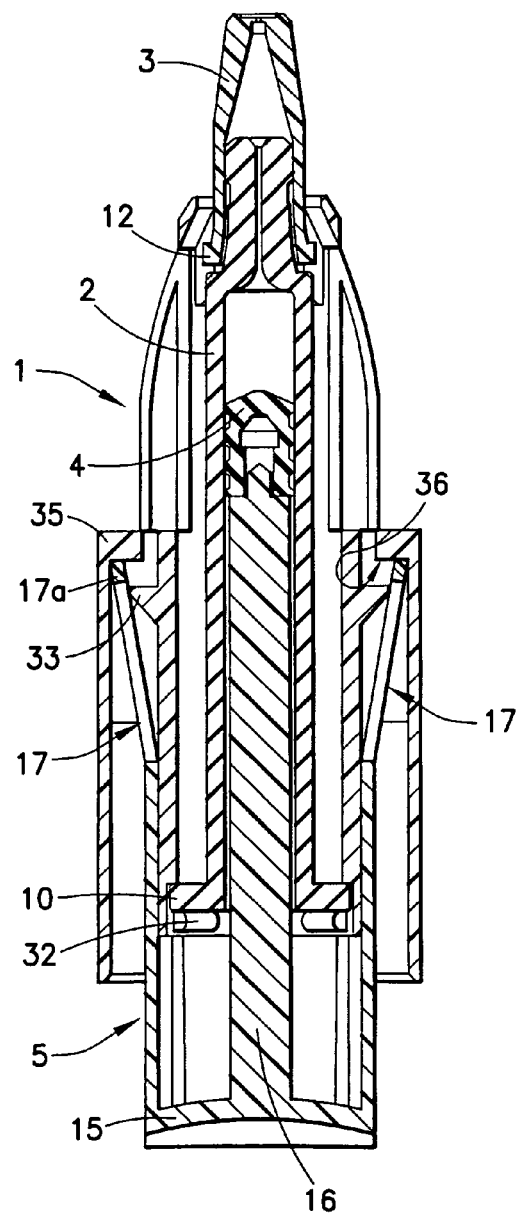

The continuation of the movement of the pusher 5 brings the heads 17a of the tabs 17 into abutment against the stops 36, as shown in FIG. 6, the distance between each stop 36 and each corresponding projection 33 being such that this abutment occurs just before the projection 33 arrives completely opposite the window 22.

The abutment of the tabs 17 against the stops 36 keeps the tabs 17 in said second, outer radial position when the projections 33 are completely opposite the respective windows 22, under the effect of the pressure, the sliding of the pusher 5 remaining blocked with respect to the casing 6, thus marking the end, of the spraying of the first dose.

Figure 7:
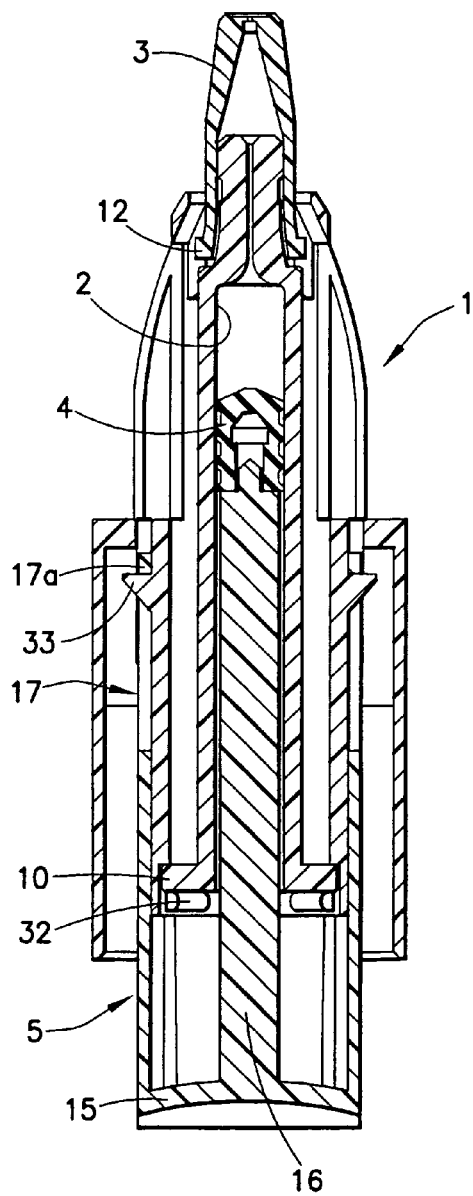
Figure 8:
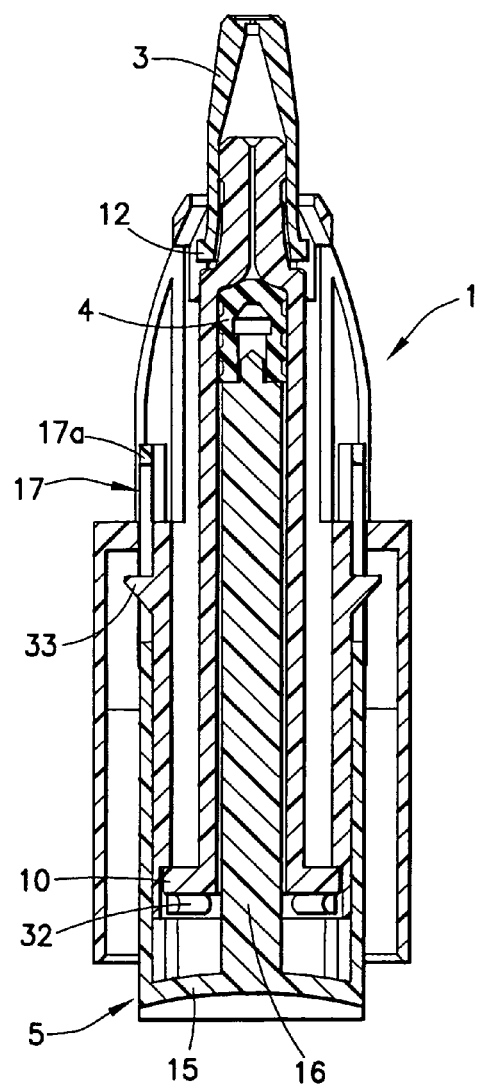

Release of the pressure exerted on the pusher 5 and therefore on the outer tabs 40 elastically frees this pressing of the heads 17a against the stops 36 and consequently allows the tabs 17 to return to their first inner radial position, as shown in FIG. 7.

Pressure may then be exerted again on the pusher 5 with an opposing force on the outer tabs 40 in order to start spraying the second dose. The lug 21 is then just below the corresponding boss 38, such that there is a second hard point having to be crossed in order to start this second spraying. Once this hard point is crossed, the second spraying may take place, the tabs 17 sliding through the openings 37 and the projections 33 sliding through the windows 22, to the end-of-spraying position shown in FIG. 8.

Figure 9:
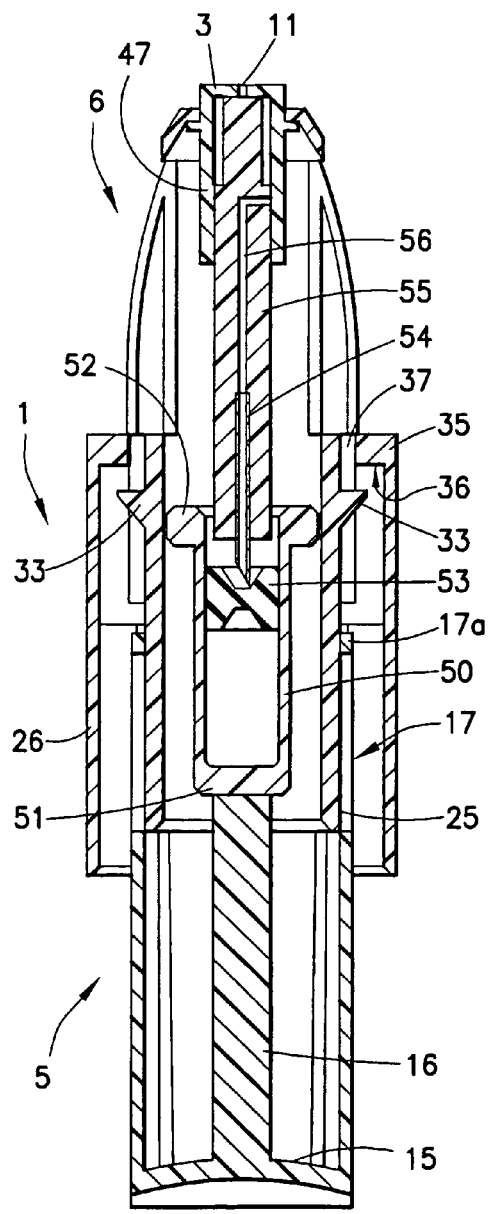
FIGS. 9 and 10 are views thereof in axial section of the device according to the invention according to two variants of the first embodiment, respectively.
Figure 10:
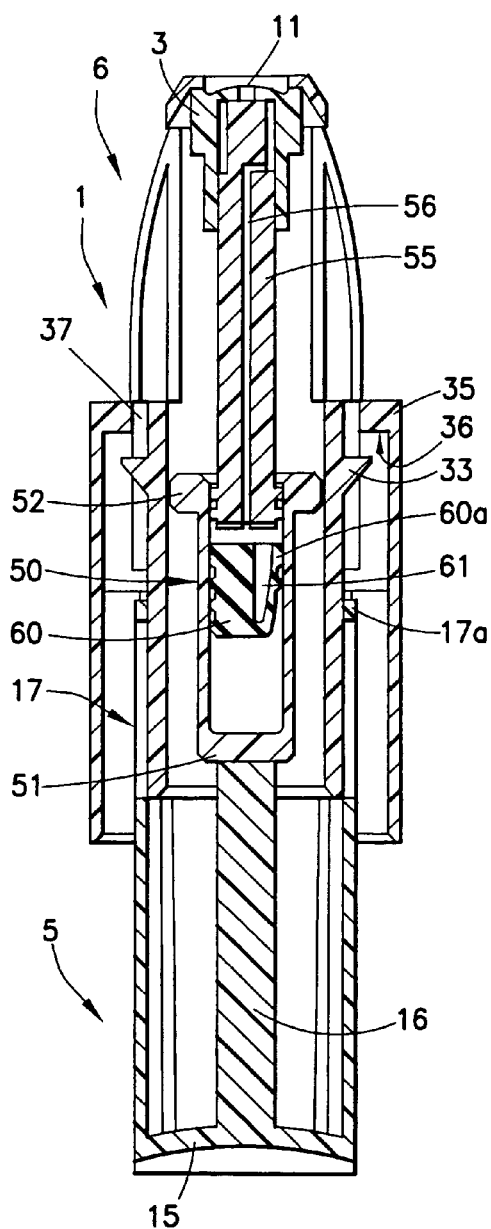

FIGS. 9 and 10 show a device 1 very similar to that which has just been described. The elements already described with reference to FIGS. 1 to 8, which are found again in this device and which are functionally identical or equivalent, are denoted by the same numerical references and will not be described again.

In the case of FIG. 9, the device 1 comprises a container 50 of the carpule type, with a proximal bottom 51 and a distal collar 52, a plunger 53 having a thinned central region, a hollow needle 54 suitable for piercing this thinned central region, and a rod 55 held by a spray nozzle 3 mounted on the casing 6, this rod 55 comprising the needle 54 and forming a flow conduit 56 for the product.

In practice, the central rod 16 of the pusher 5 bears against the bottom 51 of the container 50, which moves the container 50 and the plunger 53 until the needle 54 pierces the thinned central region of the plunger 53, thus allowing the liquid product of interest to flow.

In the case of FIG. 10, the device 1 comprises a container 50 identical to that of the device shown in FIG. 9 and a rod 55 similar to that comprised in this device, but without a needle 54. The plunger 60 then comprises an axial recess 61, opening out in its distal face and made on one side of this plunger 60, this recess 61 thus defining a side wall portion 60a of the plunger 60 having flexibility in the radial direction of this plunger. This wall 60a moves aside under the pressure of the product resulting from the pressing of the rod 55 against the plunger 60 following the movement of the container 50 with respect to the rod 55, thus freeing the flow of the product.

Figure 11:
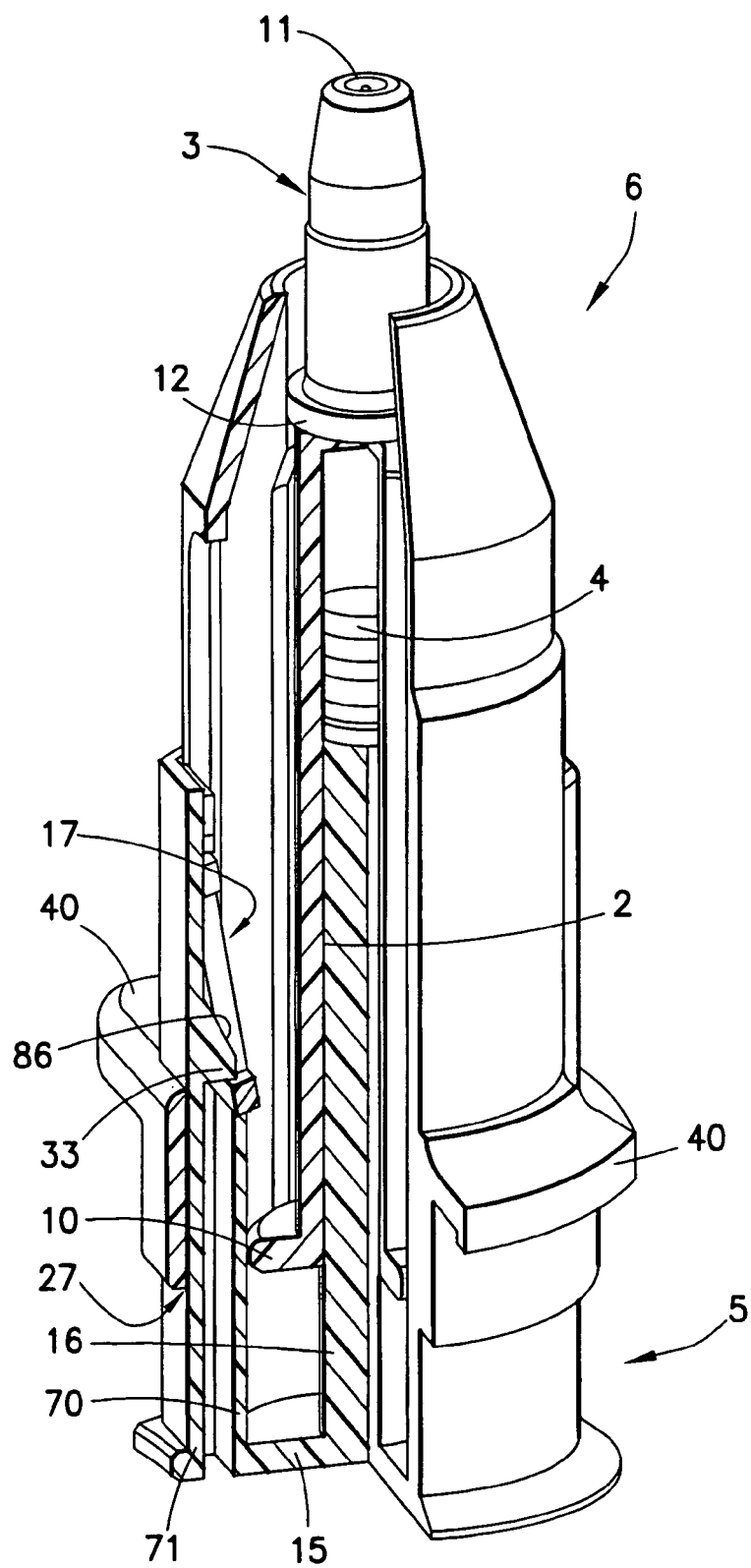
FIG. 11 is a view thereof in axial section over a sector, of a device according to the second embodiment of the invention.

FIG. 11 shows a device 1 similar to that described with reference to FIGS. 1 to 8, according to a second embodiment of the invention. The tabs 17 are made on the casing 6 and the projections 33 and the stops 36 are made on the pusher 5. In this case also, the elements already described with reference to FIGS. 1 to 8, which are found in this device and which are structural and/or functionally identical or equivalent, are denoted by the same numerical references and will not be described again.

In this case, the pusher 5 comprises an inner wall 70 in which are formed the stops 36, and an outer wall 71, defining between them the openings 37. The wall 71 comprises the projections 33, each comprising a ramp 86, and extends beyond these projections 33, this wall 71 being engaged in the space 27 defined between an inner wall 25 of the casing 6 and an outer wall 26 of this same casing; connecting the tabs 40 together.

Figure 12:
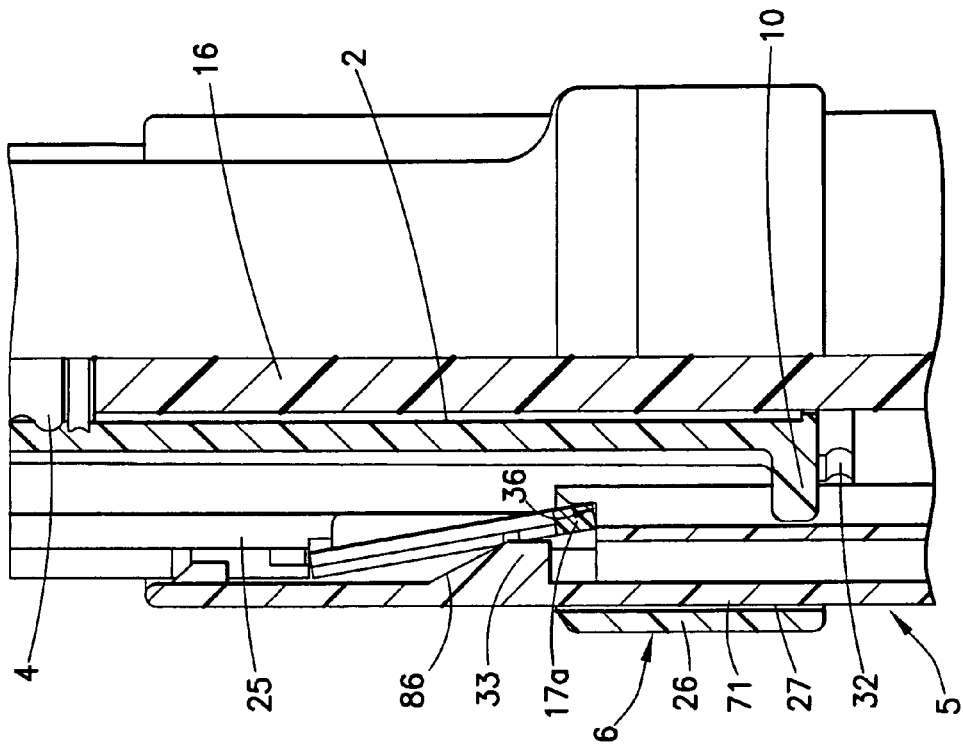
FIGS. 12 to 15 are partial views thereof in axial half-section, respectively at the start of injecting a first dose, at the end of injecting this first dose, at the start of injecting the second dose and at the end of injecting this second dose, according to the second embodiment
Figure 13:
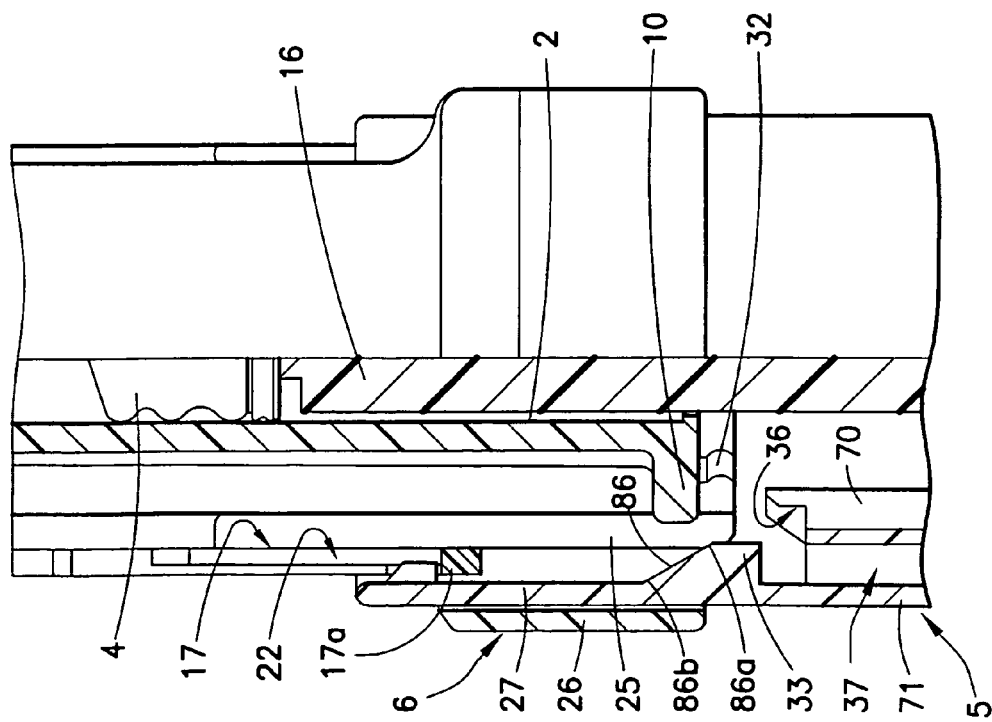
Figure 15:
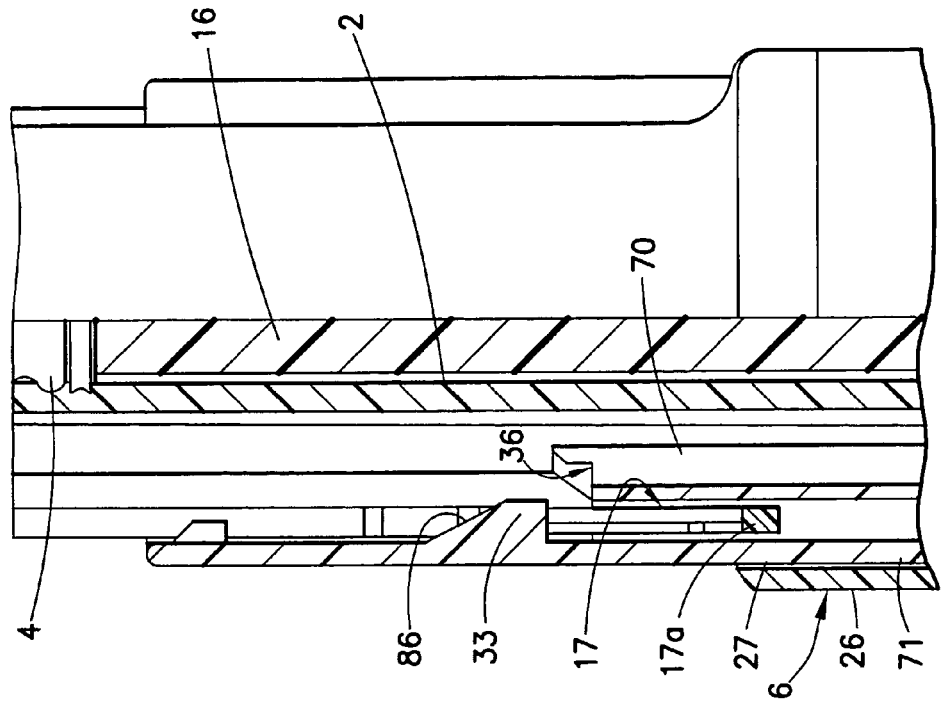
Figure 14:
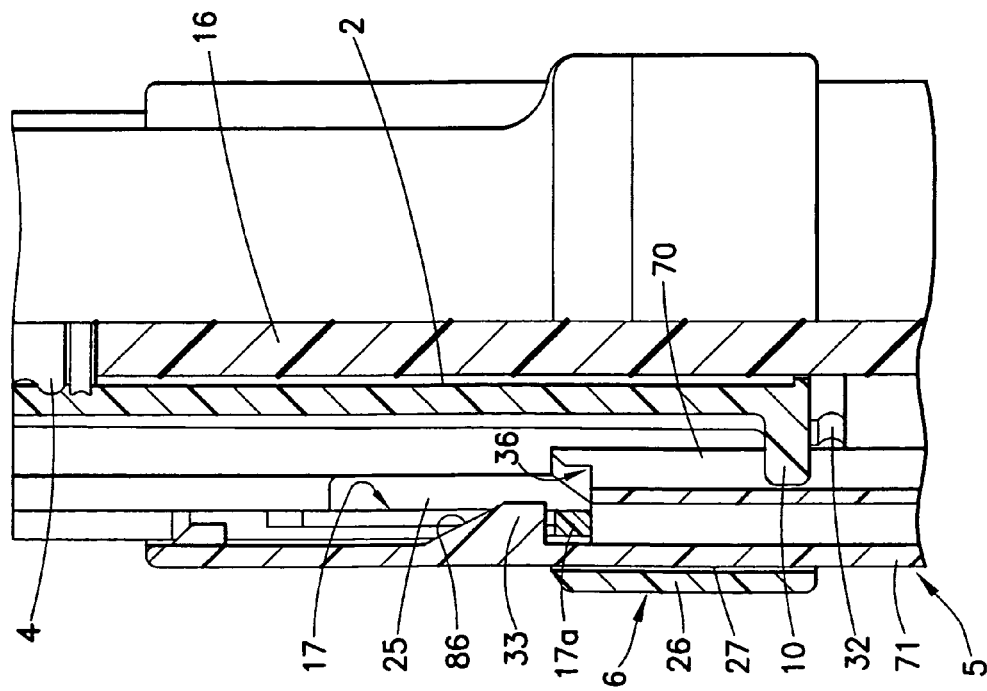

The tabs 17 are formed by cuts made on each side in said inner wall 25. In a manner similar to that which has been described above, when spraying the first dose (cf. FIG. 12), the movement of the pusher 5 with respect to the casing 6 causes the projections 33 to move the tabs 17, and more particularly the heads 17a, with respect to the ramps 86, toward said second radial position (in this case, inner position) until these tabs 17 abut against the stops 36 (cf. FIG. 13); following release of the force exerted on the pusher 5, the tabs 17 return to said first radial position (cf. FIG. 14), which makes it possible to continue spraying the second dose, the tabs 17 engaging in the openings 37, and the projections 33 in the windows 22, until the end of this spraying (cf. FIG. 15).

The means for controlling the length of travel of the pusher 5 with respect to the casing 6, which are common to the first two embodiments of the present invention, those according to FIGS. 1 and 11 respectively, therefore comprise:

at least one tab (17) arranged on the pusher (5) or the casing (6), able to move between a first, unstressed, normal position in which said tab does not block the axial movement of the pusher, and a stressed, flexed, second position in which said tab halts the axial movement of the pusher, said tab at its free end comprising a pressing region or element (17a) designed to contribute both to the halting of the axial movement of the pusher (5) and to the flexing of the tab (17) under the effect of the axial movement of the pusher, at least one ramp (86) cooperating with said tab from an initial end (86a) to a final end (86b) and arranged respectively on the casing (6) or on the pusher (5), against which the pressing region or element (17a) of said tab (17) bears in the direction of pressure of said pusher (5), said ramp being designed to bring said tab from its normal first position to its flexed second position, at least one stop (36) cooperating with the pressing region or element (17a) of the tab (17), arranged respectively on the casing (6) or the pusher (5), respectively beyond or before the final end (86b) of the ramp (86) in the direction of pressure, against which the pressing region or element (17a) of the tab (17) finally abuts in its flexed second position, at least one nonpressing region or opening (22) which is arranged on the tab (17) before or beyond said pressing region or element (17a), depending on whether said tab is arranged on the pusher (5) or on the casing (6), said nonpressing region or opening (22) being designed to allow said pressing region or element (17a) to return to its unstressed normal position from the halted and flexed position of the tab (17) when the pressure on the pusher (5) is released, the first portion of travel of the pusher (5) being determined by the movement of this pusher as far as its axial stop position, following contact between the pressing region or element (17a) and the stop (36), and the second portion of travel being determined by the movement of the pusher beyond the axial position in which the nonpressing region or opening (22) has accommodated the pressing region or element (17a).

Figure 16:
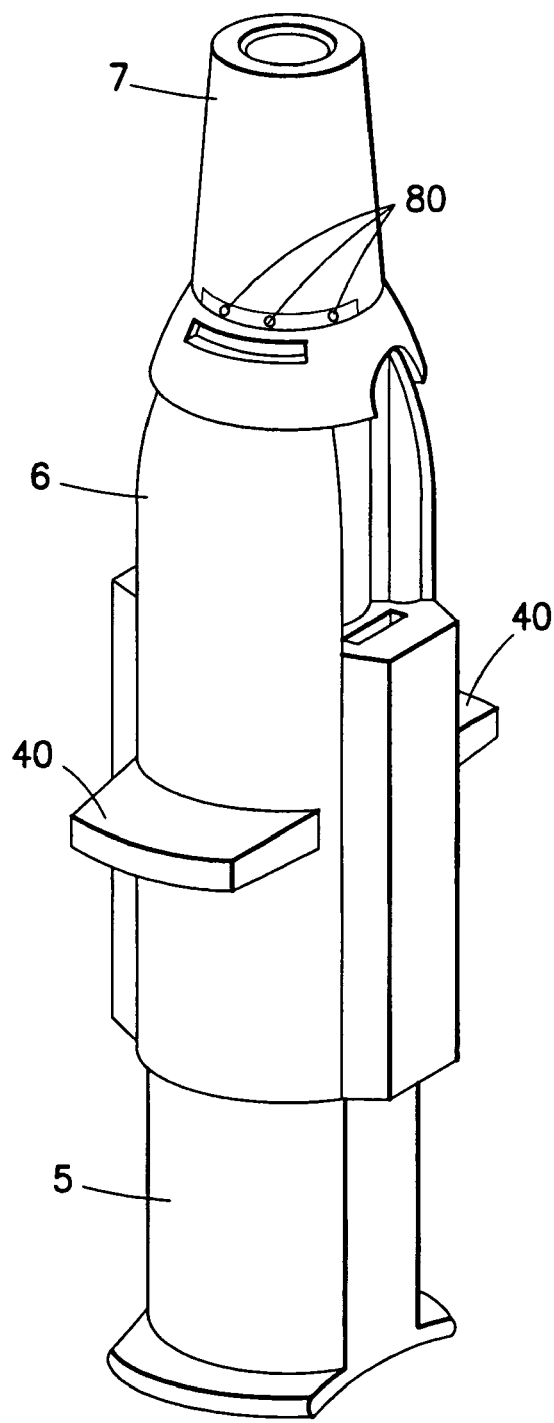
FIG. 16 is a view of a third variant of the first embodiment of the invention.

FIG. 16 shows a device 1 similar to the first embodiment, except that it comprises a lid 7 connected to the casing 6 by breakable bridges 80. These bridges 80 make it possible to force the user to have a deliberate action of use and to prevent this use being too easy for children.

Figure 20:
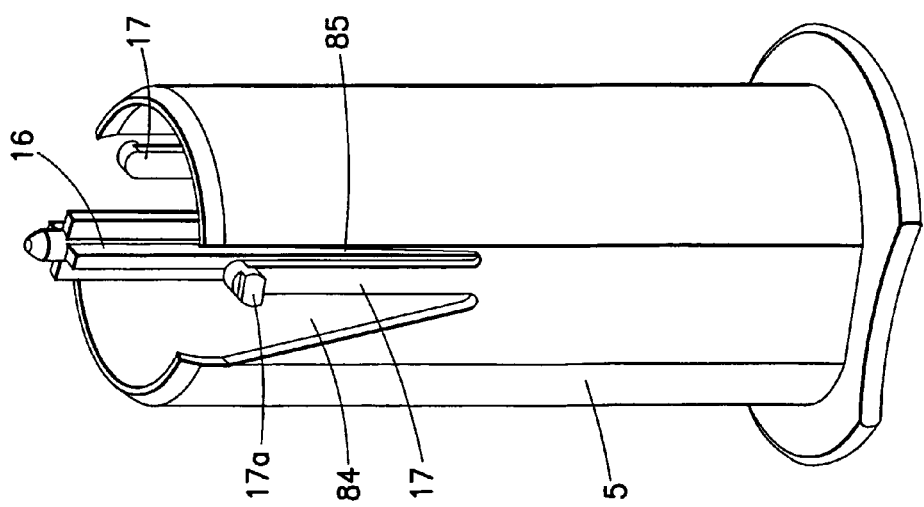
FIG. 20 is a perspective view of the pusher of the device according to FIG. 18.
Figure 22:
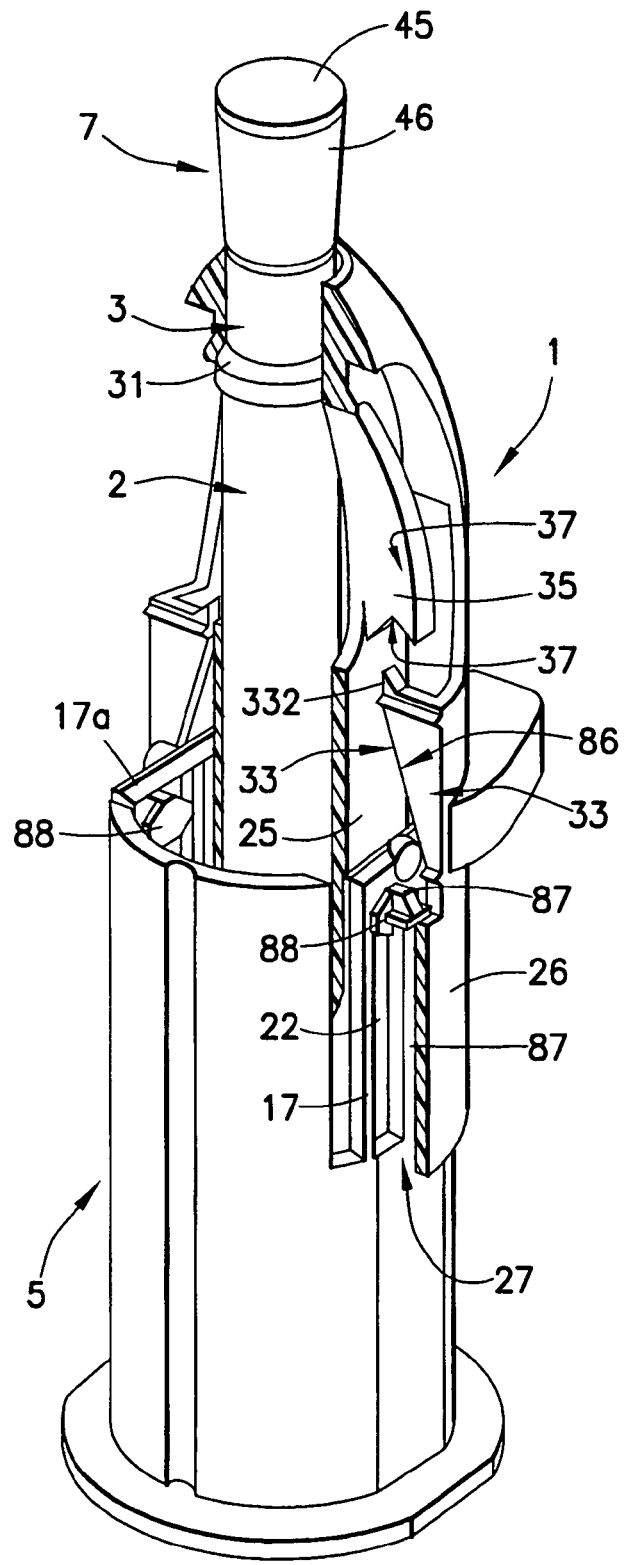
FIG. 22 shows, in perspective, with partial section, a device according to a fourth embodiment of the invention.
Figure 23:
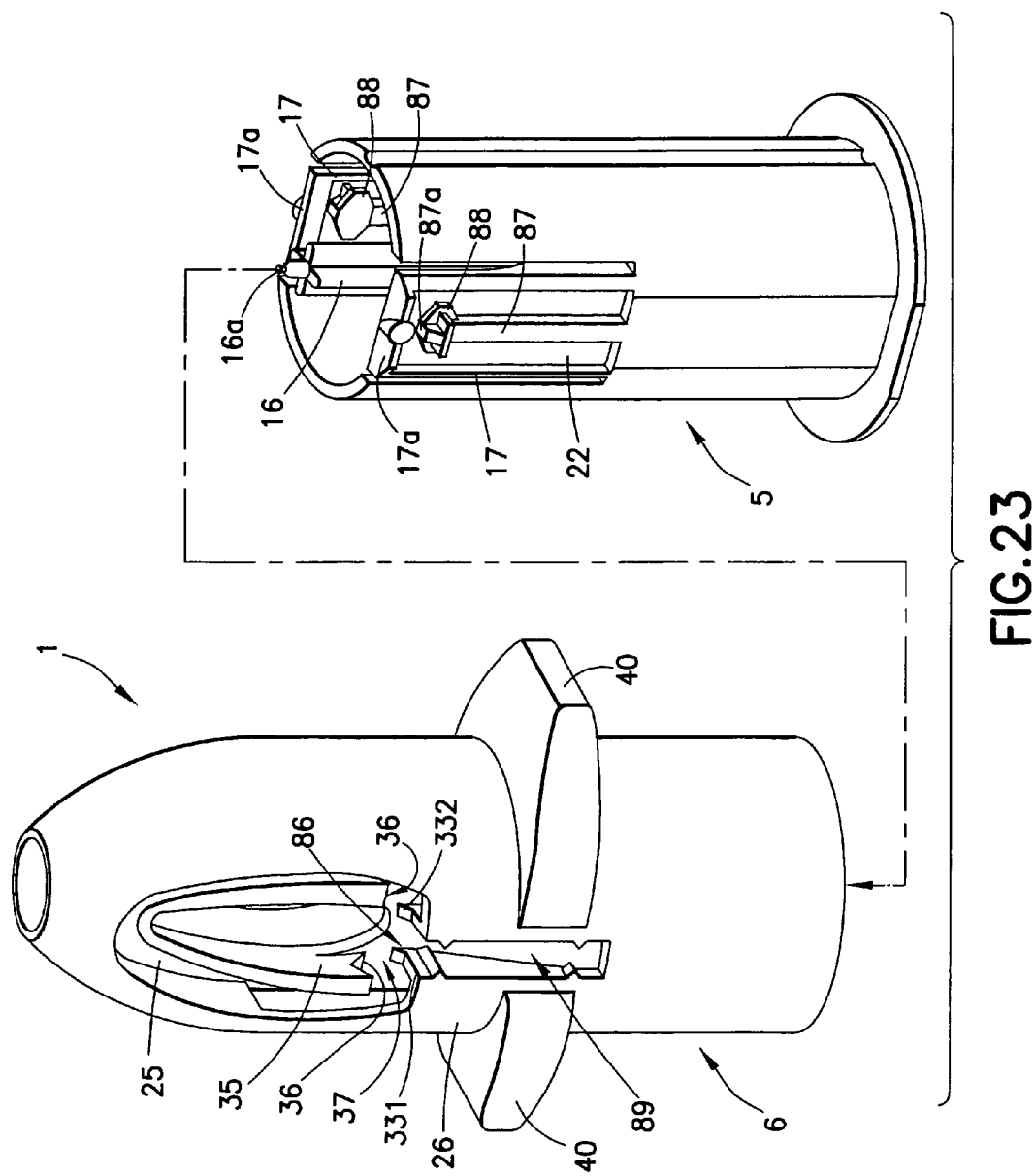
FIG. 23 shows, in perspective, and separately, the casing and the pusher of the device according to FIG. 22.

A third embodiment of a device according to the invention, characterized in particular in that the flexed second position of the tabs 17 is obtained by tangential stress, is now described with reference to FIGS. 18 to 20.

According to this third embodiment of the present invention, as was the case with the first embodiment previously described, the tabs 17 are arranged on, the pusher 5, while the ramp 86 is arranged on the casing 6, in the form of a continuous groove passing through the wail of said casing.

The nonpressing opening 22, belonging to the through groove, is arranged on the casing 6, before the stop 36, also belonging to said through groove, when the tab 17 is arranged on the pusher 5 (as already indicated) and the pressing element 17a specified hereinbelow cooperates with the hollow ramp 86 formed on the casing 6.

Figure 21:
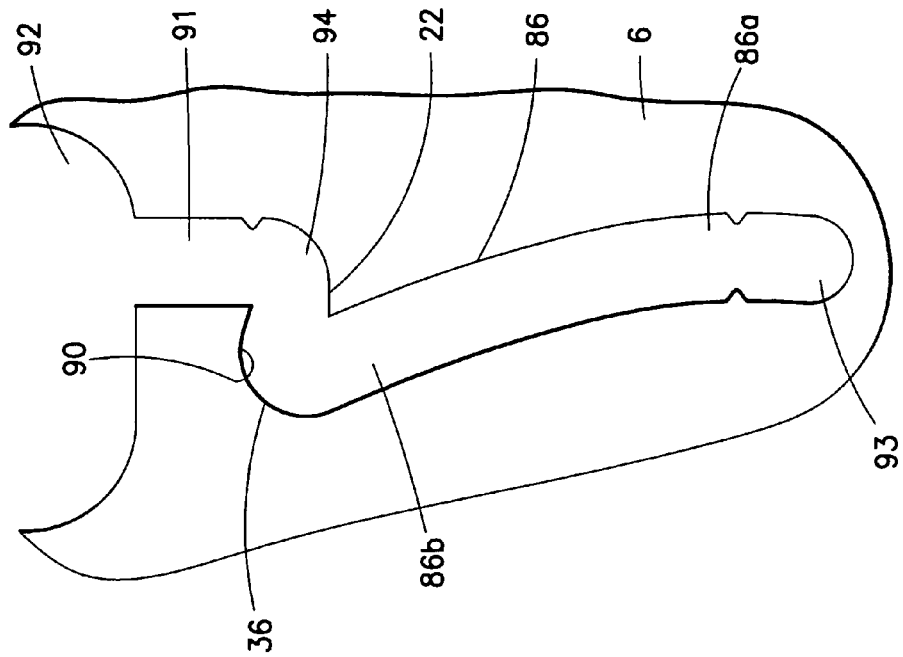
FIG. 21 is an enlarged view, laid out flat, of the ramp belonging to the casing according to FIG. 19.

Each tab 17 arranged on the pusher 5 at its free end comprises a stud 17a forming a pressing element or region extending transversely toward the casing 6. A V-shaped cut 84, anterior with respect to the tab 17, allows the latter to deflect tangentially from its normal first position to its flexed second position. The ramp 86 arranged on the casing 6 is arranged in a hollow, or such that it passes through, so as to accommodate the stud 17a and extends more or less obliquely (compare FIG. 21) in the wall of the casing 6, from the initial end 86a to the final end 86b. The stop 36 discussed in the previous forms of embodiment of the invention cooperates with the stud 17a, it is arranged on the casing 6 beyond the final end 86b of the ramp 86 and is determined by the joining at an angle, but with continuity, of the ramp 86 with ramp return 90, of inverse slope with respect to the actual ramp 86 proper. The nonpressing region or opening 22 discussed earlier is arranged in a hollow on the casing 6, before the abovementioned stop 36, in continuity with the ramp 86 and the ramp return 90; this non-pressing region 22 is designed to accommodate the stud 17a when the tab 17 returns to its normal position from its halted and flexed position. Further, an axial slot 91 extends in continuity from the previously described nonpressing region 22 but beyond the latter. The axial slot 91 in the casing 6 opens out freely into a through opening 92 of the casing 6, forming a window through the outer wall of said casing; it being understood that, according to this third embodiment of the invention, the second portion of travel of the pusher 5 is determined by the abutment of the plunger against the wall of the container 2.

Before the initial end 86a of the ramp 86, and continuous therewith, a housing 93 in which to park the stud 17 is formed. The snap-fitting of the stud 17a into the housing 93 allows definitive assembly of the pusher 5 and of the casing 6.

Beyond the nonpressing region or opening 22, and in continuity therewith, a housing 94 for parking the stud 17a is formed, like the housing 93, in the outer wall of the casing 6.

The third embodiment of the invention already described gives greater robustness and a smaller axial size. This embodiment also guarantees effective halting of the pusher with respect to the casing between the two portions of the travel of said pusher, and therefore before the second dose of the product of interest is delivered.

A fourth and final embodiment of the present invention, which is like the first or second embodiment already described, is now described with reference to FIGS. 22 to 30.

Figure 25:
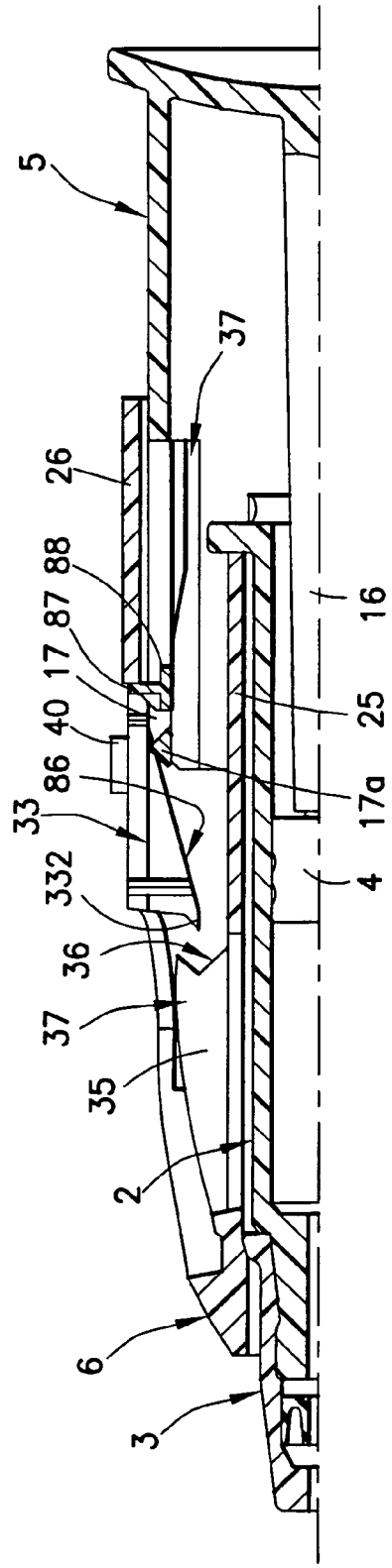
Figure 26:
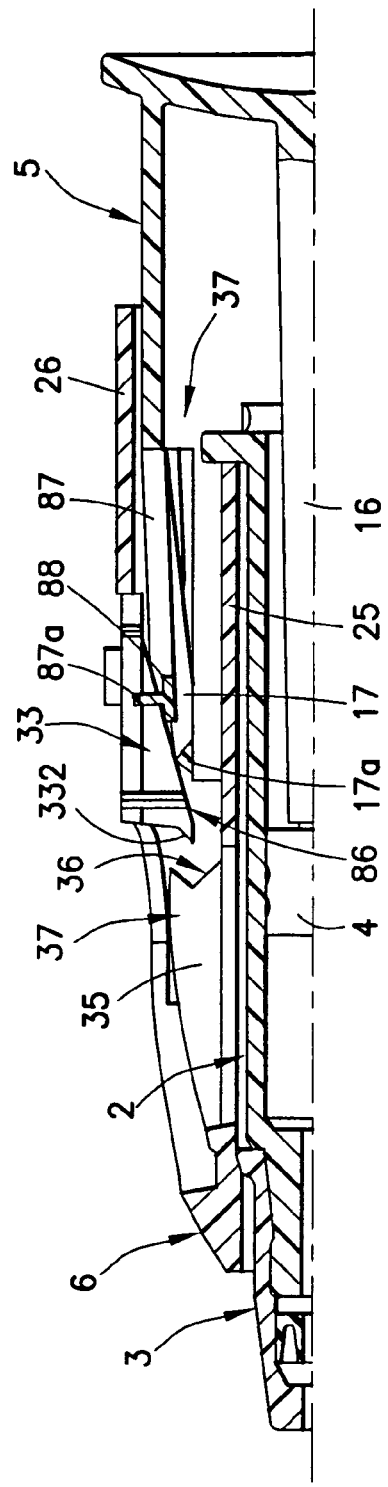

At least one tongue 87, separate from or independent of the tab 17, is arranged, as the case may be, on either the pusher 5 or the casing 6, depending on whether the tab 17 is itself arranged on the pusher 5 or the casing 6, respectively. This tongue 87 can move between an unstressed normal first position in which said tongue does not in general impede the axial movement of the pusher during the two successive portions of travel thereof, and a stressed flexed second position in which said tongue 87 plays a part in returning the pusher 5, in the opposite direction to the pressure, and does so in order to allow the tab or tabs 17 to return to their normal position from their flexed halted position. As shown in perspective in FIG. 23, but more explicitly in FIGS. 25 to 30, the ramp 86 and the free end 87a of the tongue 87 are designed to cooperate with one another so that during the first portion of travel of the pusher, for example at the end thereof, the tongue 87 finds itself flexed (compare FIG. 27), and during the second portion of travel of the pusher the tongue 87 escapes the ramp 86 and returns to its normal position (compare FIGS. 29 and 30). The unstressed normal first position of the tongue 87 is shown in FIG. 25, while a stressed flexed second position is shown in FIGS. 26 to 28.

According to FIGS. 22 to 30, the flexed second position of the tongue 87 is obtained by radial stress when the flexed second position of the tabs 17 is itself obtained by radial stress also. It must be understood that, in a way which has not been depicted, this flexed second position of the tongue 87 could be obtained by tangential stress, while the flexed second position of the tabs 17 would itself be obtained by tangential stress.

Each tab 17, arranged, as the case may be, on the pusher 5 or the casing 6, comprises a nonpressing window 22 of overall rectangular shape, at the center of which the tongue 87 extends parallel to the axis of the device. As in the other embodiments of the invention, the ramp 86 belongs to a projection 33 arranged, as the case may be, on the casing 6 or on the pusher 5, which ramp is designed to pass freely through the window 22. The stop 36 is arranged, on the casing 6 or the pusher 5, as the case may be, such that when each tab 17 is in the flexed second position, the projection 33 comes to face the window 22 then penetrates through this window when the pressure on the pusher 5 is released, thus causing each tab 17 to return to its first position.

More specifically, each tongue 87 is arranged at the center of the window 22 with its free end, 87a remaining before the head 17a or pressing region of the corresponding tab. The free end 87a comprises two ears 88 for pressing against the ramp 86. The latter comprises two parallel flanges 331 and 332 arranged on each side of a slot 89, which allows the tongue 87 free passage in translation. Each ear 88 is designed to come into contact with a ramp portion 86 defined by a flange 331 or 332 and to do so in the direction of pressure of the pusher 5; beyond the first portion of travel of the pusher 5, each ear 88 escapes from the corresponding ramp portion or flanges 331 or 332 so that the tongue 87 returns to the normal position.

Figure 24:
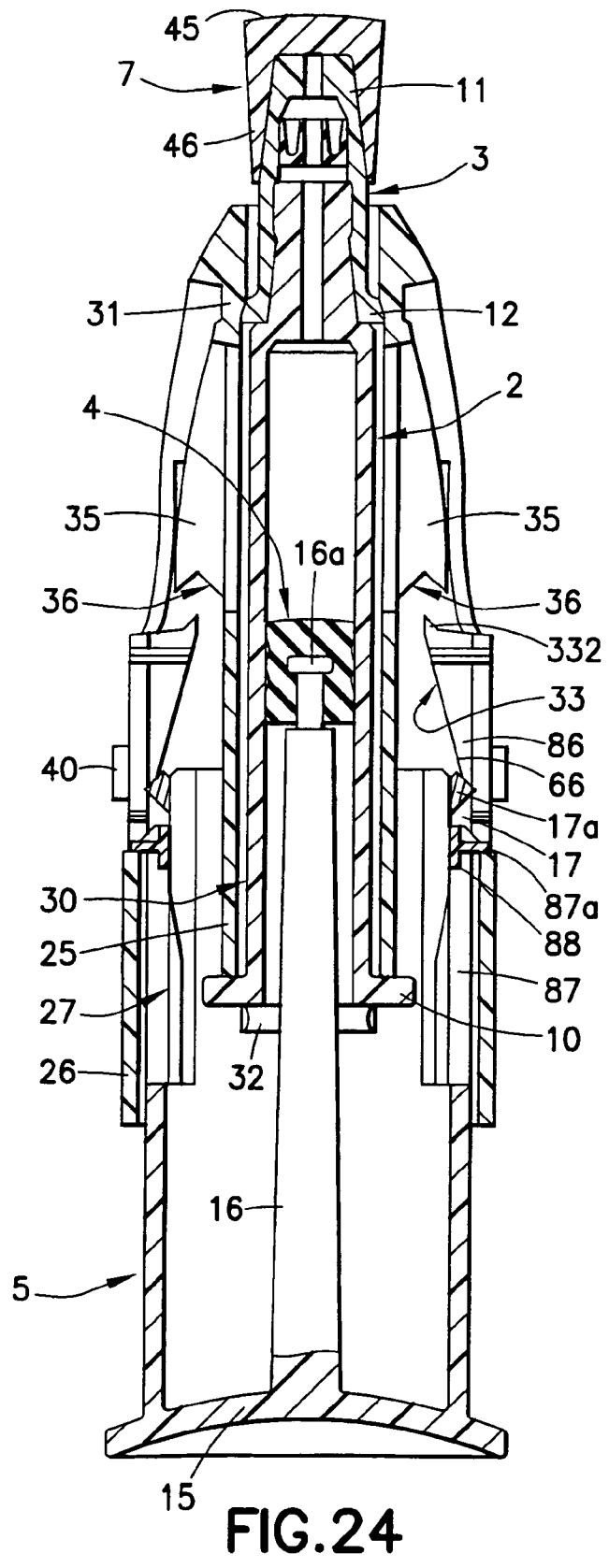
FIG. 24 shows a view in axial section of the device according to FIG. 22.

In the initial position of the pusher 5 with respect to the casing 6, which position is shown in FIG. 24, the tab 17 and the tongue 87 are in their normal, radial, and unstressed, position.

According to FIG. 26, by pressure on the pusher 5, the movement of the head 17a of the tab 17 causes this tab to flex without in any way, to start with, causing the corresponding tongue 87 to flex, such flexing occurs at the end of the travel of the head 17a.

According to FIG. 27, by continuing the movement of the pusher 5, the tab 17 is fully flexed whereas the ears 88, in contact with the ramp 33 and more specifically with the flanges 331 and 332, respectively, flexing the corresponding tongue 87, by virtue of the nonpressing region or opening 22, by continuing the pressure of the pusher 5, the tab 17 escapes the ramp 86, or projection 33, the corresponding tongue 87 remaining flexed, the flexed tongue 87 exerts on the ramp 86 an antagonistic pressure that contributes to the return of the pusher 5, in the opposite direction to the pressure, when this pressure is released. In consequence, the tongue 87 returns to a flexed intermediate position; cf. FIG. 28.

Starting out from the relative position of the casing and of the pusher which have been shown, in FIG. 28, by resuming the pressure on the pusher 5, the free end 87a of the tongue 87 in contact with the ramp 86 immediately escapes the latter (cf. FIG. 29) so that the pusher 5 can be pushed beyond the relative position shown by FIG. 28, in order to deliver the second dose of the product of interest; cf. FIG. 30.

As is apparent from the above, the invention provides a decisive improvement to the prior art, by providing a device which is easy to manipulate, while reducing errors of use to a minimum and retaining a structure which is relatively simple and inexpensive to manufacture.

It goes without saying that the invention is not limited to the embodiment described above by way of example but that, on the contrary, it covers all the variant embodiments that fall with respect to the field of protection defined by the claims appended hereto. The syringe body 2 and the spray nozzle 3 may especially be manufactured as a single part.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps, which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A spray or injection device for spraying or injecting a product of interest, in liquid form, the device being configured to deliver at least a first and a second preset dose of the product in succession, the device extending along a reference axis from a distal end to a proximal end, the device comprising:
   an axially elongate container containing the product;
   a plunger disposed in and blocking off the container, the plunger being axially moveable with respect to the container, in a reference direction, and allowing the product to be propelled distally from the container;
   a casing configured to accommodate and axially secure the container, the casing having a stop surface; and
   a pusher assembled with the casing such that the pusher and casing are moveable with respect to each other, the pusher configured to move the plunger within the container in the reference direction and having a stop surface which engages the stop surface of the casing to form a stop enclosed by the casing when the plunger is advanced a certain distance in the container, the stop defining a length of travel of the pusher with respect to the casing so as to divide the length of travel of the pusher into a first travel portion corresponding to the delivery of the first preset dose, and a second travel portion corresponding to the delivery of the second preset dose;
   wherein the stop surface of the pusher and the stop surface of the casing are configured to allow disengagement therebetween when a force applied to the pusher in the reference direction is reduced and, without any rotational movement of the pusher or casing, the pusher can then be advanced along the second travel portion for delivery of the second preset dose.

2. The device as claimed in claim 1, further comprising at least one tab arranged on the pusher or the casing, and configured to move between a first, unstressed, normal position in which the tab does not block the axial movement of the pusher, and a stressed, flexed, second position in which the tab halts the axial movement of the pusher, the tab at a free end defining the stop surface of the pusher or casing, respectfully, and comprising a pressing region or element configured to contribute both to the halting of the axial movement of the pusher and to the flexing of the tab under the effect of the axial movement of the pusher;
   at least one ramp cooperating with the tab from an initial end to a final end, and arranged respectively on the casing or on the pusher the ramp being configured to bring the tab from the normal first position to the flexed second position as the plunger is moved in the container to allow contact of the pusher stop surface with the casing stop surface;
   the stop surface of the casing or pusher cooperating with the pressing region or element of the tab, and arranged respectively on the casing or the pusher, respectively, to allow return of the tab to the first, unstressed, normal position when the force applied to the pusher in the reference direction is reduced.

3. The device as claimed in claim 2, wherein the stressed, flexed, second position of the tab is obtained by radial stress.

4. The device as claimed in claim 3, wherein the tab arranged on the pusher or the casing comprises a nonpressing window set back with respect to the pressing region or element, wherein the ramp is included in a projection arranged respectively on the casing or the pusher and configured to pass freely through the window, the projection faces the window of the tab, and penetrates through the window when the pressure on the pusher is released, causing the tab to return to the first position.

5. The device as claimed in claim 2, wherein the stressed, flexed, second position of the tab is obtained by tangential stress.

6. The device as claimed in claim 2, further comprising at least one tongue distinct from or independent of the tab, arranged on the pusher or the casing depending on whether the tab is arranged on the pusher or on the casing, configured to move between an unstressed, normal, first position in which the tongue does not impede the axial movement of the pusher and a stressed flexed second position in which the tongue contributes to returning the pusher to allow the tab to return to the normal, first position from the flexed and halted position, and wherein the ramp and the free end of the tongue are configured to cooperate with one another such that, during the first portion of travel of the pusher, the tongue is flexed, and during the second portion of travel of the pusher, the tongue escapes from the ramp and returns to the normal position.

7. The device as claimed in claim 6, wherein the flexed second position of the tongue is obtained by radial stress when the flexed second position of the tab is obtained by radial stress.

8. The device as claimed in claim 6, wherein the flexed second position of the tongue is obtained by tangential stress when the flexed second position of the tab is obtained by tangential stress.

9. The device as claimed in claim 2, further comprising at least two tabs and two projections.

10. The device as claimed in claim 2, wherein the casing and the pusher comprise at least one hard point that must be crossed at the start of delivering a dose.

11. The device as claimed in claim 10, the hard point comprises at least one lug projecting laterally from the tab and at least one boss.

12. The device as claimed in claim 2, wherein the pusher is made from a flexible plastic, the mobility of the tab resulting from the flexibility of the pusher, the tab is not deformed in the first radial position and the tab is elastically deformed in the second radial position.

13. The device as claimed in claim 2, wherein the tab has a distal head with projecting edges, forming, with a complementary means disposed in the casing, snap-fastening means making it possible to prevent the separation of the pusher from the casing after the engagement of the pusher in the casing.

14. The device as claimed in claim 1, wherein the container is formed by a syringe body comprising a proximal collar and a distal flow conduit, the syringe body comprising a spray nozzle fitted onto a distal end of the syringe body, which forms a spray head making it possible to spray the product contained in the syringe body.

* * * * *